US012690750B2

(12) United States Patent (10) Patent No.: US 12,690,750 B2

Au et al. (45) Date of Patent: Jul. 28, 2026

(54) BOW SPRING DRIVEN SUCTION VALVE FOR AN ENDOSCOPE

(71) Applicant: Boston Scientific Scimed, Inc., Maple Grove, MN (US)

(72) Inventors: Yu Him Michael Au, Framingham, MA (US); Annika Hsu, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 191 days.

(21) Appl. No.: 18/604,123

(22) Filed: Mar. 13, 2024

(65) Prior Publication Data

US 2024/0306886 A1     Sep. 19, 2024

Related U.S. Application Data

(60) Provisional application No. 63/490,130, filed on Mar. 14, 2023.

(51) Int. Cl.
*A61B 1/015* (2006.01)
*A61B 1/00* (2006.01)

(52) U.S. Cl.
CPC ...... *A61B 1/00068* (2013.01); *A61B 1/00066* (2013.01); *A61B 1/015* (2013.01)

(58) Field of Classification Search
CPC . A61B 1/00068; A61B 1/00094; A61B 1/015; A61B 1/12; A61B 1/00066
See application file for complete search history.

(56) References Cited

U.S. PATENT DOCUMENTS

2020/0352415 A1* 11/2020 Harris ................ A61B 1/00068
2020/0375434 A1* 12/2020 Scutti ..................... A61B 1/015
2021/0378486 A1  12/2021 McCabe
2022/0221069 A1   7/2022 Ng
2025/0009205 A1*  1/2025 Harada .............. A61B 1/00006

FOREIGN PATENT DOCUMENTS

DE      102020129207 A1     5/2022

OTHER PUBLICATIONS

International Search Report and Written Opinion dated Jul. 1, 2024 for International Application No. PCT/US2024/019727.

* cited by examiner

*Primary Examiner* — Michael J Carey
*Assistant Examiner* — Olivia Grace Starkey
(74) *Attorney, Agent, or Firm* — Seager, Tufte & Wickhem, LLP

(57) ABSTRACT

Devices, systems, and methods for a suction valve assembly for a medical device. The suction valve assembly may include a valve body with a valve well and a bow spring within the valve well. A cap is connected to the bow spring that, when actuated, flexes the bow spring to open the valve. When released, the bow spring unflexes and closes the valve.

20 Claims, 5 Drawing Sheets

BOW SPRING DRIVEN SUCTION VALVE FOR AN ENDOSCOPE

CROSS-REFERENCE TO RELATED APPLICATIONS

This application claims the benefit of U.S. Provisional Patent Application Ser. No. 63/490,130 filed on Mar. 14, 2023, the disclosure of which is incorporated herein by reference.

TECHNICAL FIELD

This disclosure relates generally to valve assemblies and methods, and particularly to suction valve assemblies and methods for an endoscope.

BACKGROUND

A wide variety of intracorporeal medical devices and systems have been developed for medical use, for example, for endoscopic procedures. Some of these devices and systems include guidewires, catheters, catheter systems, endoscopic instruments, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices and systems as well as alternative methods for manufacturing and using medical devices and systems.

SUMMARY

This disclosure provides design, material, manufacturing method, and use alternatives for medical devices and medical systems. In a first example, a suction valve assembly for a medical device can comprise a valve body having a valve well, an inlet channel in fluid communication with the valve well, and an outlet channel in fluid communication with the valve well; and a bow spring configured to move within the valve well, comprising a central arc having inner and outer sides, such that the bow spring, when flexed, moves the central arc towards the outer side, a valve stem attached to the inner side of the central arc of the bow spring. The bow spring can be positioned with the inner surface of the central arc facing the inlet channel of the valve body such that the bow spring, when unflexed, presses the stem into the inlet channel to close the valve. The bow spring, when flexed, can pull the stem away from the inlet channel to open the valve.

Alternatively or additionally to any of the examples above, the suction valve assembly can further include a cap accessible from outside the valve body, the cap in mechanical communication with the bow spring such that actuating the cap flexes the bow spring and releasing the cap unflexes the bow spring.

Alternatively or additionally to any of the examples above, the cap comprises a projection extending into the valve well in contact with the bow spring.

Alternatively or additionally to any of the examples above, the valve well extends the length of the longest dimension of the valve body between a top face and an opposing bottom face of the valve body, and the inlet and outlet channels are positioned in side surfaces of the valve well.

Alternatively or additionally to any of the examples above, the valve well comprises a curved wall and a flat wall each extending between a top face and an opposing bottom face of the valve body, and one or more of the bow spring and the cap comprise a shaped portion abutting at least the flat wall to prevent rotation within the valve body.

Alternatively or additionally to any of the examples above, a top anchor of the bow spring and a bottom anchor of the bow spring are each shaped portions of the bow spring abutting the flat wall of the valve well to prevent rotation of the bow spring within the valve body.

Alternatively or additionally to any of the examples above, a flange of the cap is a shaped portion of the cap abutting the flat wall of the valve well to prevent rotation of the flange within the valve well.

Alternatively or additionally to any of the examples above, the suction valve assembly further includes a circumferential seal disposed about the valve stem that presses against the inlet opening when the valve is closed.

Alternatively or additionally to any of the examples above, the main body further comprises a collar at an upper opening of the valve well; and the cap further comprises a clip in contact with the collar of the main body when the valve is in a closed position.

Alternatively or additionally to any of the examples above, the bow spring further comprises an anchor having an inclined bottom surface, and the valve well further comprises an inclined floor surface mirroring the shape and angle of the inclined bottom surface of the bow spring anchor such that the inclined bottom surface and the inclined floor surface meet within the valve well.

Alternatively or additionally to any of the examples above, the main body comprises a single piece of uniform material.

Alternatively or additionally to any of the examples above, the cap comprises a single piece of uniform material.

Alternatively or additionally to any of the examples above, the bow spring comprises a single piece of uniform material.

Alternatively or additionally to any of the examples above, the cap, the main body, and the bow spring are made of polyethylene plastic.

In another example, an endoscopic surgical device comprises an endoscopic probe, a suction valve assembly according to any of the examples above, and a source of suction in fluid communication with the inlet channel of the suction valve assembly, such that opening the valve provides suction to the endoscopic probe from the inlet channel, through the valve well, and into the outlet channel. The outlet passage of the suction valve assembly is in fluid communication with the endoscopic probe.

In another example, a suction valve assembly can be for use in an endoscope having a lumen configured to extend into a patient's body cavity. The suction valve assembly comprises a valve body having a valve well, an inlet channel in fluid communication with the valve well, and an outlet channel in fluid communication with the valve well; and a bow spring configured to move within the valve well, comprising a central arc having inner and outer sides, such that the bow spring, when flexed, moves the central arc towards the outer side, a valve stem attached to the inner side of the central arc of the bow spring. The bow spring is positioned with the inner surface of the central arc facing the inlet channel of the valve body such that the bow spring, when unflexed, presses the stem into the inlet channel to close the valve. The bow spring, when flexed, pulls the stem away from the inlet channel to open the valve.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various embodiments and together with the description serve to explain the principles of the present disclosure.

Figure 1:
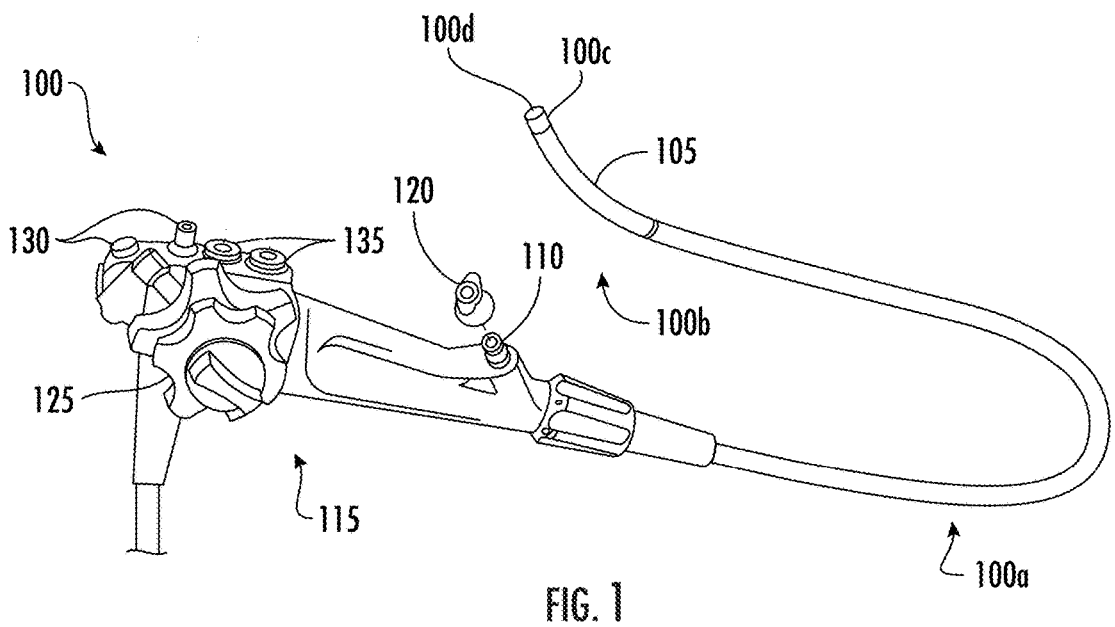
FIG. 1 depicts a schematic view of components of an illustrative endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an illustrative medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is illustrative only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The detailed description is intended to illustrate but not limit the disclosure Those skilled in the art will recognize that the various elements described may be arranged in various combinations and configurations without departing from the scope of the disclosure. The detailed description illustrates example embodiments of the disclosure.

Figure 2:
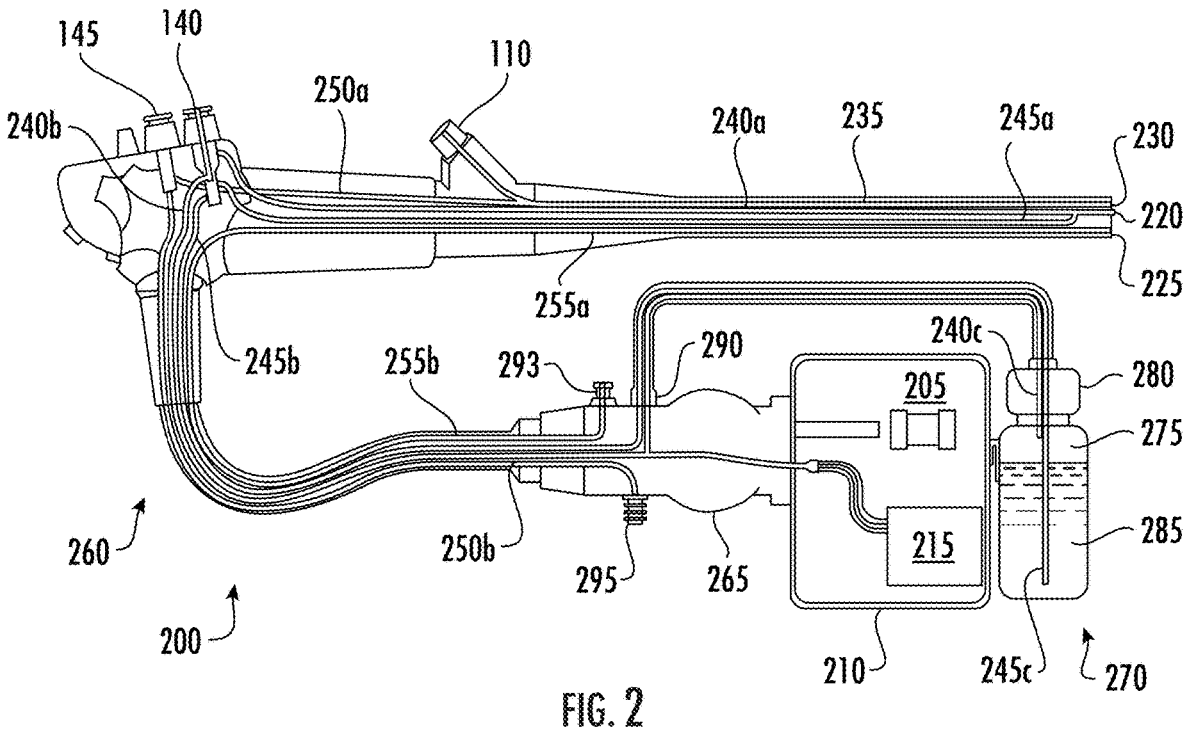
FIG. 2 depicts a schematic view of components of an illustrative endoscope system.

With reference to FIG. 1, an illustrative endoscope 100 is depicted and FIG. 2 depicts an illustrative endoscope system 200. The endoscope 100 may include an elongated tube or shaft 100*a* that is configured to be inserted into a subject (e.g., a patient).

A light source 205 of the endoscope system 200 may feed illumination light to a distal portion 100*b* of the endoscope 100. The distal portion 100*b* of the endoscope 100 may house an imager (e.g., CCD or CMOS imager) (not shown). The light source 205 (e.g., lamp) may be located in a video processing unit 210 that processes signals input from the imager and outputs processed video signals to a video monitor (not shown) for viewing. The video processing unit 210 may also serve as a component of an air/water feed circuit by housing a pressurizing pump 215, such as an air feed pump, in the unit 210.

The endoscope shaft 100*a* may include a distal tip 100*c* (e.g., a distal tip unit) provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 may extend along the shaft 100*a* to a proximal channel opening 110 positioned distal to an operating handle 115 (e.g., a proximal handle) of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115.

The handle 115 may be provided with dual valve locations 135. One of the valve locations 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2).

The other valve location 135 may receive a suction valve 145 for operating a suction operation. A suction supply line 250*a* may run distally from the suction valve 145 along the shaft 100*a* to a junction point in fluid communication with the working channel 235 of the endoscope 100.

The operating handle 115 may be electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) may be fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, may pass through the top 280 of the reservoir 270 to the same detachable connection 290 as the gas supply tubing 240*c* on the connector portion 265. In other embodiments, the connections may be separate and/or separated from each other. The connector portion 265 may also have a detachable irrigation connection 293 for irrigation supply tubing (not shown) running from a source of irrigation water (not shown) to the irrigation feed line 255*b* in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100.

The gas feed line 240*b* and lens wash feed line 245*b* may be fluidly connected to the valve location 135 for the gas/water valve 140 and configured such that operation of the gas/water valve in the well controls supply of gas or lens wash to the distal tip 100*c* of the endoscope 100. The suction feed line 250*b* is fluidly connected to the valve location 135 for the suction valve 145 and configured such that operation of the suction valve 145 in the well controls suction applied to the working channel 235 of the endoscope 100.

The suction valve 145 may be configured to allow or prevent suction and/or a suction effect in the working channel 235. When the suction valve 145 is in a valve closed position (e.g., a first configuration), a suction fluid flow through the working channel 235 may be blocked by the suction valve 145. When suction is desired in the working channel 235, an operator or user may actuate the suction valve 145 (e.g., by depressing a button on the valve and/or actuating the suction valve 145 in one or more other suitable manners) in order to bring the suction valve 145 to a valve open position (e.g., a second configuration). When the suction valve 145 is in the valve opened position, a flow channel inside the suction valve may connect the working channel 235 to the suction device coupled to suction connection 295 and the suction device may create a negative pressure that draws fluid into and out of the working channel 235 through an outlet provided in the suction valve. When the operator or user releases the suction valve 145, the valve 145 may return to its valve closed position and reduce or block a suction fluid flow from the working channel 235.

In some cases, suction valves 145 may rely on a path of least resistance to direct suction fluid flow through the endoscope system 200. In some cases, when a suction pump is turned on for a procedure, the pump remains on for an entirety of the procedure and continually pulls air from the flexible umbilical 260, which in turn draws fluid from the line side of the endoscope 100 that runs up the umbilicus 260 and connects to a port at the suction valve 145. When the suction valve 145 is in a first position and/or configuration (e.g., a closed position) the suction force or negative pressure from the suction pump is blocked from the working channel 235 and may pull fluid from atmosphere through the suction valve 145. When the suction valve 145 is actuated to a second position and/or configuration (e.g., an opened position) (e.g., when the button or cap associated with the suction valve 145 is depressed and/or actuated in one or more other suitable manners), the opening from atmosphere through the suction valve 145 to the suction pump may be effectively closed or blocked by the suction valve 145 and a fluid path between working channel 235 and the suction pump through the suction valve 145 may be opened. Thus, fluid moving to the suction pump may follow a path of least resistance, where the path may change depending on whether the suction valve 145 is in a first position (e.g., a closed position) or a second position (e.g., an opened position)

In some cases, valve stems of suction valves 145 may be configured to have a close fit with a valve well configured to receive the valve stem in the endoscope 100. In such suction valves 145, when the valve stem is in a first position the close fit blocks a flow path or increases a resistance to flow between the working channel 235 and the suction pump and reduces a resistance to flow between atmosphere and the suction pump. Similarly, when the valve stem is in a second position, the close fit blocks a flow path or increases a resistance to flow between the atmosphere and the suction pump and reduces a resistance to flow between the working channel 235 and the suction pump.

Suction valves 145 configured to block flow using close fits between the valve stem and valve well requires valves stems that are precisely manufactured. The precision required to produce suction valves with close fits requires expensive materials (e.g., metals, etc.), highly precise machinery, and is time consuming to achieve.

Additionally, suction valves 145 with close fit valve stems and valve wells are manufactured to have at least some clearance to allow the valve stem to adjust positions within the valve well. This clearance, may result in leakage during use, which may lead to two issues noticeable by a physician. The first is when the suction valve 145 is in a position intended to block suction from the working channel 235, there is still some suction flow passing through the working channel 235 and the suction valve 145 to the suction pump. The smaller the clearance between the valve stem and the valve well, the less unwanted flow through the working channel 235 that occurs and the larger the clearance, the more unwanted flow through the working channel 235, however, clearance is needed to facilitate movement of the valve stem within the valve well. When flow is actively moving up the working channel 235 in such configurations of the suction valve 235, users may perceive the suction as "poor insufflation" due to the suction of the suction pump pulling volume from a body lumen in which the user is working, even when the suction valve 145 is in a position intended to block a suction flow from the working channel 235. Second, when a valve stem of the suction valve 145 is in a position within a valve well to facilitate a suction flow between the working channel 235 and the suction pump through the suction valve 145, the flow from atmosphere to the suction pump may not be completely blocked. Any such leaking from atmosphere may reduce a pressure differential between suction valve and the distal end of the working channel 235, which leads to a reduced suction force or negative pressure, reduced flow rates, and aerated flow through the fluid path to the suction pump.

Suction valves 145 configured to operate with close-fit valve stems and valve wells may work well enough when intended for re-use in multiple procedures, as a price point for such suction valves can be high enough to justify manufacturing the suction valves 145 from materials and with the necessary precision that can achieve and maintain desired tolerances over the life of the reusable suction valves 145. However, a price point of a single use suction valve may not allow for use of the necessary materials, tools, and/or precise manufacturing required to achieve and/or maintain tolerances over the life of single-use suction valves.

Figure 3A:
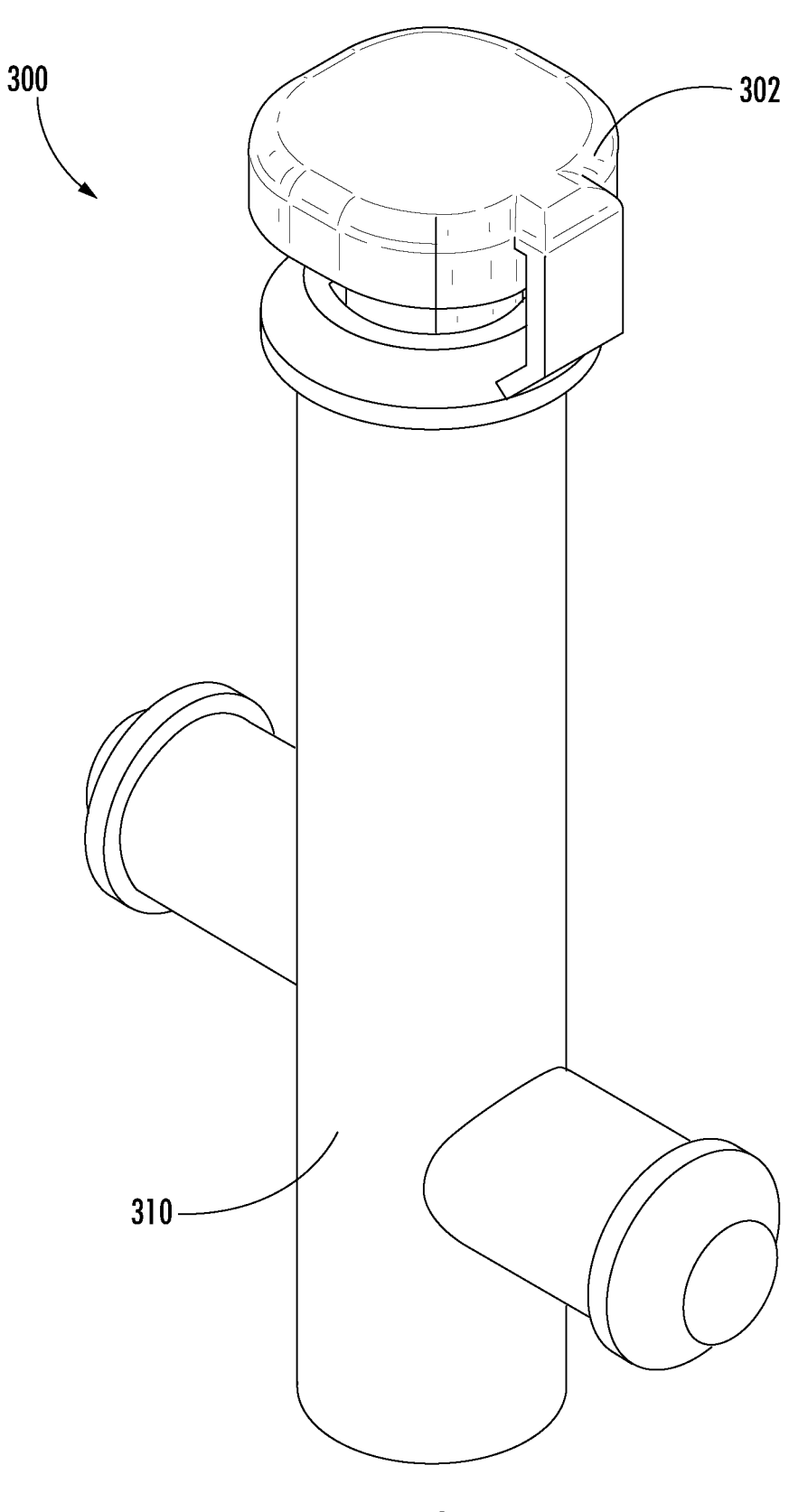
FIG. 3A depicts a schematic perspective view of an illustrative suction valve.
Figure 3B:
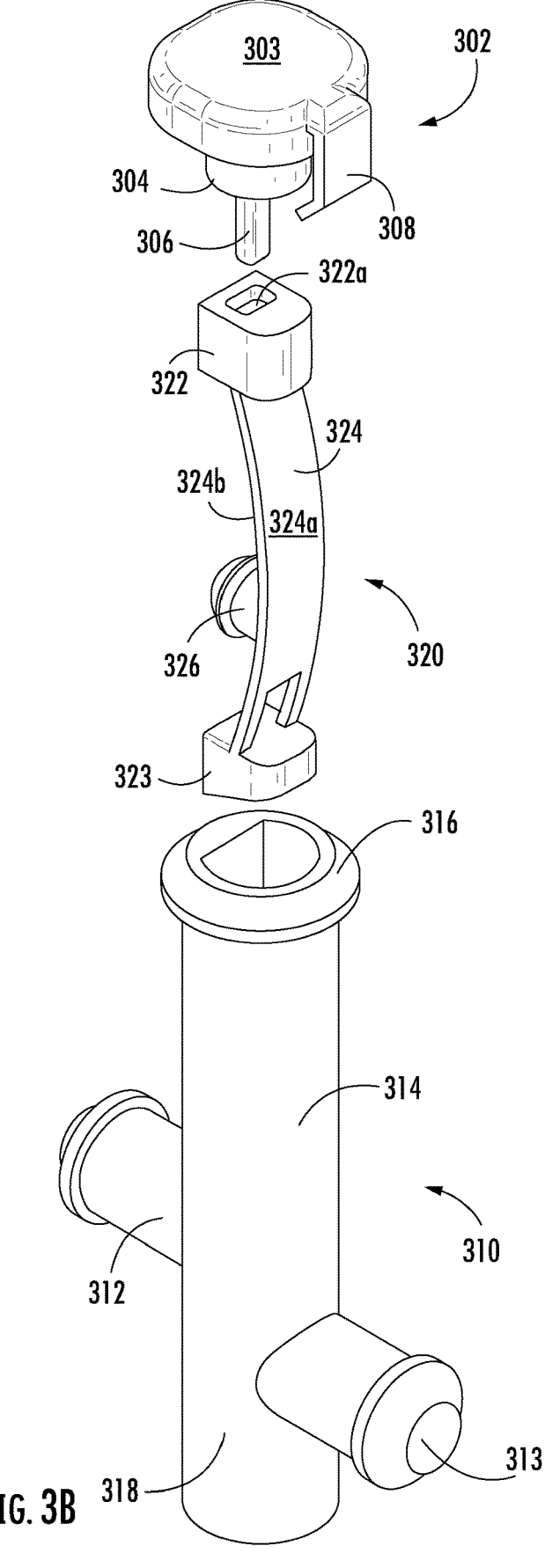
FIG. 3B depicts and exploded perspective view of the illustrative suction valve of FIG. 3A.

The suction valve configurations for endoscopes 100 and/or other suitable scopes discussed herein address the above-noted concerns with existing suction valves and are configured to mitigate and/or eliminate leakage along an unintended flow path through the suction valve 145. FIGS. 3A and 3B depict a schematic perspective view of an illustrative suction valve 300 configured to address these concerns.

As shown in FIGS. 3A and 3B, the suction valve 300 includes a cap 302, a main body 310, and a bow spring 320. The main body 310 houses the bow spring 320, which is in mechanical communication with the cap 302 seated above and inserted into the main body 310.

The main body 310 defines an inlet channel 312, an outlet channel 313, and a valve well 314. A collar 316 at the top of the main body 310 interfaces with the cap 302. A floor surface 318 at the bottom of the valve well 314 provides an anchoring surface for the bow spring 320.

The cap 302 has a broad button surface 303 that is pressed by a user to actuate the valve 300, a flange 304 that fits within the valve well 314 of the main body 310, a projection 306 that interfaces with the bow spring 320, and a clip 308 that further interfaces with the main body 310 to secure the cap 302.

The bow spring 320 has top and bottom anchors 322 and 323, a central arc 324 with an outer surface 324a and an inner surface 324b, and a valve stem 326 on the inner surface 324b of the arc 324. The top anchor 322 has a recess 322a to receive the projection 306 of the cap, while the bottom surface of the bottom anchor 324 is shaped to contact the floor surface 318 of the main body 310.

Figure 4:
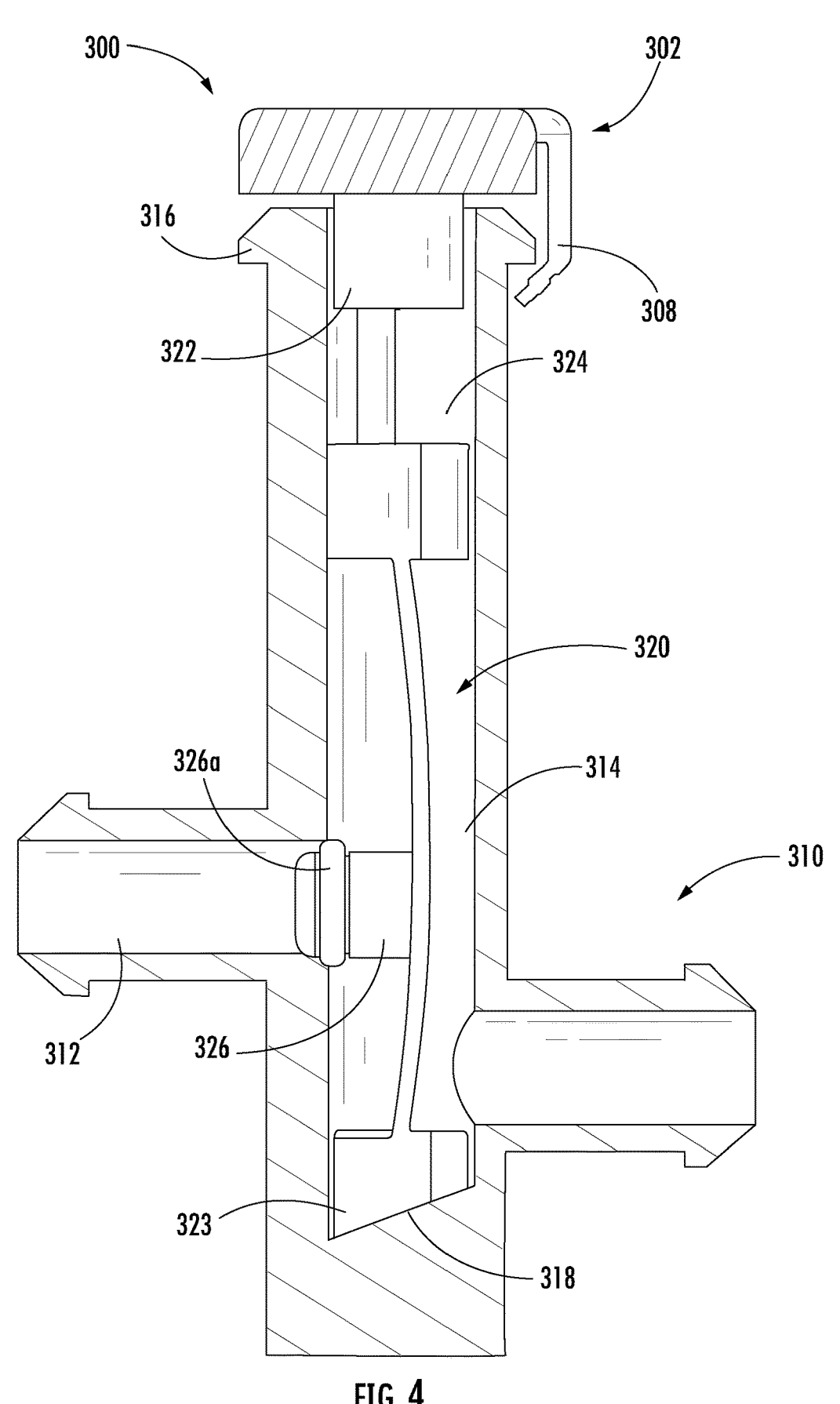
FIG. 4 depicts a schematic cross-section view of an illustrative suction valve, with the suction valve in a first configuration.

As shown in FIG. 4, when not being pressed, the cap 302 is disposed in an upward position. The clip 308 connects to the underside of the collar 316 of the main body 310 to limit the cap's upward movement. The valve stem 326 of the bow spring 320 is disposed within the inlet channel 312, which is in fluid communication with the source of suction. The valve stem's position means that the valve 300 is closed and suction will not be applied at the end of the endoscopic probe.

As shown, a seal ring 326a attached to the valve stem 326 may interface with the walls of the inlet channel 312 to assure a sufficient seal within the closed valve. The seal ring 326a may be any appropriate material, such as rubber or flexible plastic, and in some implementations may be significantly more flexible than the materials of the stem 326 and the walls of the channel 312. One of ordinary skill will recognize that the shape and size of the seal ring 326a may vary depending on the quality of the seal that is required, the overall resilience needed, and the predicted usage of the valve 300.

The central arc 324 of the bow spring 320 is shaped to unflex toward a more lengthened position, pushing against the anchors 322 and 323. The bottom anchor 323 is in contact with the floor surface 318, made of a rigid material so that the floor surface 318 will not move relative to the rest of the main body 310. Instead, the top anchor 322 will be pushed upwards, biasing the cap 302 into the unpressed position.

Figure 5:
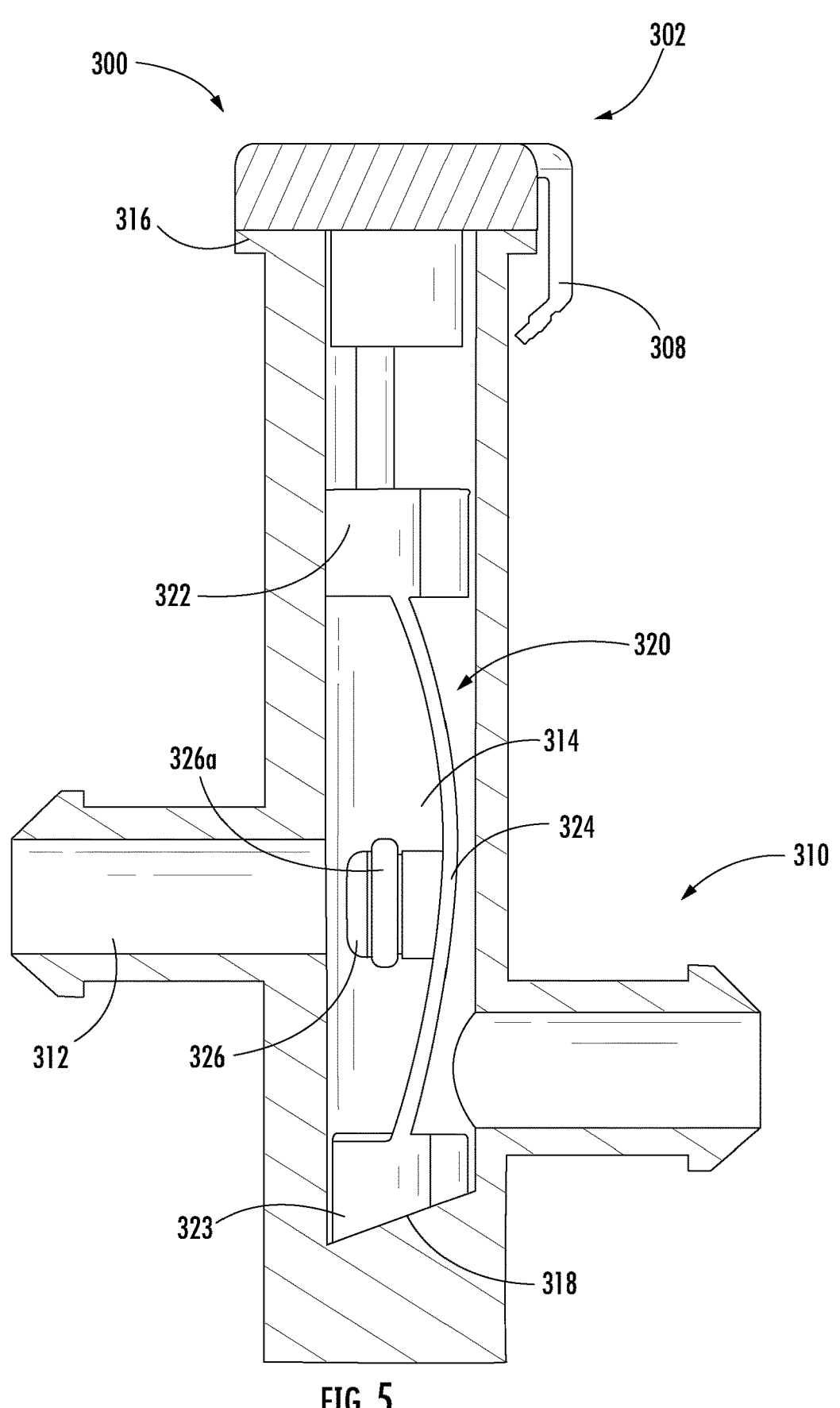
FIG. 5 depicts a schematic cross-section view of the illustrative suction valve in FIG. 4, with the suction valve in a second configuration.

As shown in FIG. 5, when a user presses down on the button surface 303 of the cap 302, the flange 304 of the cap 302 slides further into the recess of the valve well 314. When the cap 302 is fully pressed downwards, the underside of the cap 302 may be in contact with the top of the collar 316. The cap 302 in turn pushes the top anchor 322 further into the valve well, flexing the central arc 324 of the bow spring 320. This, in turn, unseats the valve stem 326 from the inlet channel 312 to open the valve 300, thus permitting suction through the valve and the attached endoscopic probe.

The cross section of the valve well 314 may be in a variety of shapes, but as shown in FIG. 3B, the cross section may be a generally circular profile with one flattened side. One of ordinary skill will recognize that such a shape can restrict rotational freedom of the valve components, thus helping to assure that the valve stem 326 stays aligned with the inlet channel 312. The flange 304 of the cap 302 and the upper and lower anchors 322, 323 of the bow spring 320 may all be shaped to fit smoothly within the cross-sectional shape of the valve well 314 and may abut sufficient side surfaces of the well to avoid rotation.

The suction valve 300 may be manufactured of relatively inexpensive materials suitable for disposal after a single use. The cap 302, main body 310, and bow spring 320 (excluding the seal 326a) may each be manufactured from a single piece of polyethylene plastic, and the seal 326a may in turn be manufactured from a single piece of flexible material (plastic, rubber, or the like). Each of the three pieces of plastic may, in some implementations, be made of the same or similar materials, with the thickness and dimensions of each piece chosen to provide the necessary resilience and hardness. For example, the main arc 324 of the bow spring 320 may be thinner than the walls of the main body 310 so that the main body stays relatively rigid while the bow spring flexes as described herein. Similarly, some give may be provided in the clip 308 of the cap 302 to allow it to snap into place when assembled, while still securing the cap 302 to the main body 310 in use. The stem 326 may include a groove or recess sized to accept the seal 326a fitting tightly around the stem 326. In some cases, the seal and the valve stem may be co-extruded and molded with one or more materials. In other cases, the valve stem may be monolithic such that the body and seals are formed from a single material using molding and/or machining techniques. Components of the valve may be made of other materials. For example, the bow spring may be made of a thin leaf of metal or any appropriately elastic material, and other components may be made of any of a variety of polymers or metals suitable to the functions described herein.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A suction valve assembly for a medical device, comprising:

a valve body having a valve well, an inlet channel in fluid communication with the valve well, and an outlet channel in fluid communication with the valve well; and a bow spring configured to move within the valve well, comprising a central arc having inner and outer sides, such that the bow spring, when flexed, moves the central arc towards the outer side, and a valve stem attached to the inner side of the central arc of the bow spring;

wherein the bow spring is positioned with the inner surface of the central arc facing the inlet channel of the valve body such that the bow spring, when unflexed, presses the valve stem into the inlet channel to close the suction valve assembly; and wherein the bow spring, when flexed, pulls the valve stem away from the inlet channel to open the suction valve assembly.

2. The suction valve assembly of claim 1, further comprising:

a cap accessible from outside the valve body, the cap in mechanical communication with the bow spring such that actuating the cap flexes the bow spring and releasing the cap unflexes the bow spring.

3. The suction valve assembly of claim 2, wherein the cap comprises a projection extending into the valve well in contact with the bow spring.

4. The suction valve assembly of claim 1, wherein the valve well extends the length of the longest dimension of the valve body between a top face and an opposing bottom face of the valve body; and wherein the inlet channel and the outlet channel are positioned in side surfaces of the valve well.

5. The suction valve assembly of claim 1, wherein the valve well comprises a curved wall and a flat wall each extending between a top face and an opposing bottom face of the valve body; and wherein one or more of the bow spring and a cap comprise a shaped portion abutting at least the flat wall to prevent rotation within the valve body.

6. The suction valve assembly of claim 5, wherein a top anchor of the bow spring and a bottom anchor of the bow spring are each shaped portions of the bow spring abutting the flat wall of the valve well to prevent rotation of the bow spring within the valve body.

7. The suction valve assembly of claim 5, wherein a flange of the cap is a shaped portion of the cap abutting the flat wall of the valve well to prevent rotation of the flange within the valve well.

8. The suction valve assembly of claim 1, further comprising a circumferential seal disposed about the valve stem that presses against the inlet opening when the suction valve assembly is closed.

9. The suction valve assembly of claim 1, the valve body further comprising a collar at an upper opening of the valve well; and a cap further comprising a clip in contact with the collar of the valve body when the suction valve assembly is in a closed position.

10. The suction valve assembly of claim 1, the bow spring further comprising an anchor having an inclined bottom surface, and the valve well further comprising an inclined floor surface mirroring a shape and an angle of the inclined bottom surface of the bow spring anchor such that the inclined bottom surface and the inclined floor surface meet within the valve well.

11. The suction valve assembly of claim 1, wherein the valve body comprises a single piece of uniform material.

12. The suction valve assembly of claim 1, wherein a cap comprises a single piece of uniform material.

13. The suction valve assembly of claim 1, wherein the bow spring comprises a single piece of uniform material.

14. The suction valve assembly of claim 1, wherein a cap, the valve body, and the bow spring are made of polyethylene plastic.

15. A suction valve assembly for use in an endoscope having a lumen configured to extend into a patient's body cavity, the suction valve assembly comprising:

a valve body having a valve well, an inlet channel in fluid communication with the valve well, and an outlet channel in fluid communication with the valve well; and a bow spring configured to move within the valve well, comprising a central arc having inner and outer sides, such that the bow spring, when flexed, moves the central arc towards the outer side, and a valve stem attached to the inner side of the central arc of the bow spring;

wherein the bow spring is positioned with the inner surface of the central arc facing the inlet channel of the valve body such that the bow spring, when unflexed, presses the valve stem into the inlet channel to close the suction valve assembly; and wherein the bow spring, when flexed, pulls the valve stem away from the inlet channel to open the suction valve assembly.

16. The suction valve assembly of claim 15, further comprising:

a cap accessible from outside the valve body, the cap in mechanical communication with the bow spring such that actuating the cap flexes the bow spring and releasing the cap unflexes the bow spring.

17. The suction valve assembly of claim 15, wherein the valve well extends the length of the longest dimension of the valve body between a top face and an opposing bottom face of the valve body; and wherein the inlet channel and the outlet channel are positioned in side surfaces of the valve well.

18. The suction valve assembly of claim 15, wherein the valve well comprises a curved wall and a flat wall each extending between a top face and an opposing bottom face of the valve body; and wherein one or more of the bow spring and a cap comprise a shaped portion abutting at least the flat wall to prevent rotation within the valve body.

19. An endoscopic surgical device, comprising:

an endoscopic probe;

a suction valve assembly, comprising:

a valve body having a valve well, an inlet channel in fluid communication with the valve well, and an outlet channel in fluid communication with the valve well, and a bow spring configured to move within the valve well, comprising a central arc having inner and outer sides, such that the bow spring, when flexed, moves the central arc towards the outer side, and a valve stem attached to the inner side of the central arc of the bow spring; and a source of suction in fluid communication with the inlet passage of the suction valve assembly, such that opening the suction valve assembly provides suction to the endoscopic probe from the inlet channel, through the valve well, and into the outlet channel.

20. The endoscopic surgical device of claim 19, wherein the bow spring of the suction valve assembly is positioned with the inner surface of the central arc facing the inlet channel of the valve body such that the bow spring, when unflexed, presses the valve stem into the inlet channel to close the suction valve assembly; and wherein the bow spring of the suction valve assembly, when flexed, pulls the valve stem away from the inlet channel to open the suction valve assembly.

* * * * *